(12) United States Patent
Mallya et al.

(10) Patent No.: US 8,041,088 B2
(45) Date of Patent: Oct. 18, 2011

(54) BRAIN IMAGE ALIGNMENT METHOD AND SYSTEM

(75) Inventors: Yogisha Mallya, Karnakata (IN); Srikanth Suryanarayanan, Karnataka (IN); Krishna Seetharam Shriram, Karnataka (IN); Rakesh Mullick, Karnataka (IN); Mitali Janardan More, Mumbai (IN)

(73) Assignee: General Electric Company, Niskayuna, NY (US)

( * ) Notice: Subject to any disclaimer, the term of this patent is extended or adjusted under 35 U.S.C. 154(b) by 1261 days.

(21) Appl. No.: 11/702,372

(22) Filed: Feb. 5, 2007

(65) Prior Publication Data
US 2008/0188741 A1 Aug. 7, 2008

(51) Int. Cl.
*G06K 9/00* (2006.01)

(52) U.S. Cl. .......................................... 382/128

(58) Field of Classification Search .................. 382/128, 382/131
See application file for complete search history.

(56) References Cited

U.S. PATENT DOCUMENTS

| | | | | |
|---|---|---|---|---|
| 6,240,308 B1 * | 5/2001 | Hardy et al. | .................. | 600/407 |
| 7,450,983 B2 * | 11/2008 | Weiss | ............................. | 600/410 |
| 7,646,898 B1 * | 1/2010 | Nowinski et al. | ............. | 382/128 |

* cited by examiner

*Primary Examiner* — Tom Y Lu
(74) *Attorney, Agent, or Firm* — Scott J. Asmus

(57) ABSTRACT

A technique for automatically labeling a CT image of the brain with anatomical information. The anatomical information is obtained from an atlas of the brain prepared from an MR image of the brain. The atlas contains image data that is referenced to the Talairach coordinate system. The atlas is aligned to the CT image and the coordinate system of the CT image data is transformed to the Talairach coordinate system. The alignment of the CT image and the atlas is performed using anatomical landmarks that are visible on both the CT image and the atlas. The CT image is then labeled automatically with the anatomical information in the atlas.

20 Claims, 4 Drawing Sheets

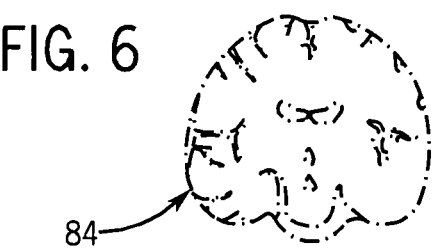
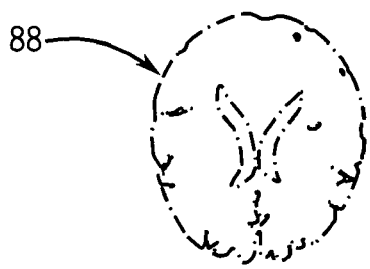
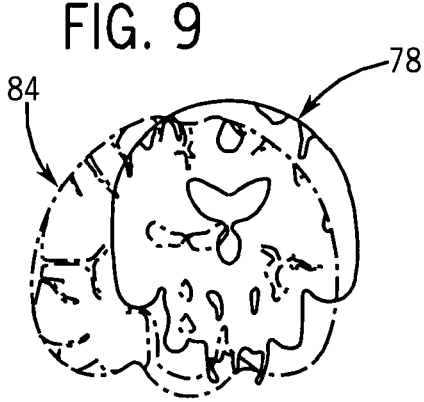
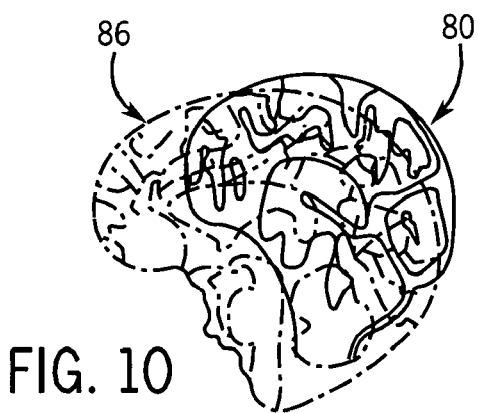
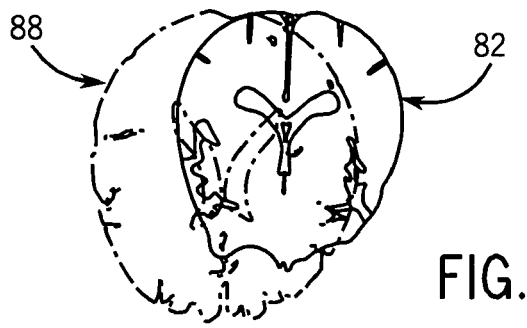

BRAIN IMAGE ALIGNMENT METHOD AND SYSTEM

BACKGROUND

The invention relates generally to medical imaging, and more particularly to a system and method for aligning a medical image of a brain to a reference atlas.

There are a variety of medical imaging systems that are currently in use that are capable of producing images of the internal anatomy of a patient. In addition to conventional X-ray machines, several technologies have been developed in recent decades that enable three-dimensional medical image data to be stored digitally. The medical image data may then be used to generate two-dimensional medical images from a variety of different perspectives. Typically the information is presented as cross-sections, or slices, of a patient's body, such as the brain.

Computed tomography (CT) is an example of a medical imaging technique that uses X-rays to create and store medical image data in three-dimensions. The patient in inserted into an aperture in a CT imaging system. An X-ray source and an X-ray detector are located on opposite sides of the patient. The X-ray source and X-ray detector are spun around the patient, while the CT imaging system takes a series of X-ray images of the patient. The CT imaging system has a computer program that uses a set of algebraic equations to estimate how much of the X-ray beam produced by the X-ray source is absorbed in the patient's body. As an approximation, the denser a material is, the whiter a volume of it will appear on the scan. Each X-ray image contains two-dimensional medical image data However, the CT imaging system is able to incorporate the two-dimensional image data and combine it in a way to form a three-dimensional model of the patient. A user may then select a desired slice (cross-section) of the three-dimensional model of the patient to be produced as a medical image. The slice may be taken at any angle relative to the body.

Magnetic resonance (MR) imaging is another imaging modality that is used to visualize the internal anatomy of a patient. However, MR imaging systems use magnetic fields, with radio frequency pulses to create images. MR is primarily used to look for structures, alterations or damage in soft living tissues, like the gray and white matter of the brain. MR imaging systems also have the ability to store imaging data in three-dimensions and for multiple slices, so that medical images of selective slices of a patient may be produced.

Each of these medical imaging methods has their various strengths and weaknesses. For example, CT systems are very good at producing images of bone, but are less useful at producing images of certain soft tissues, such as the brain. MRI systems, on the other hand, are very good at producing images of soft tissues, but are somewhat less available and can take much longer to produce an image than a CT system.

In addition, MR images of the brain are easily referenced to the Talairach atlas. The Talairach atlas is a three-dimensional coordinate system that is used to describe the location of brain structures independent of individual differences in the size and overall shape of the brain. The Talairach atlas uses the anterior commissure and the posterior commissure of the brain as reference points. The anterior and posterior commissures are fiber tracts that connect the two hemispheres of the brain. However, these anatomical features are not visible on CT images. Furthermore, there are certain risks and counter-indicators that are associated with the use of MR systems (namely as a result of the strong magnetic field that they produce) that preclude or discourage their use when the patient is unconscious, incoherent or otherwise unable to respond to questions.

Therefore, a need exists for a system or method that enables a CT system to have some of the additional benefits of an MR system without the drawbacks associated with their use.

BRIEF DESCRIPTION

A technique for automatically labeling a CT image of the brain with anatomical information is presented. The anatomical information is obtained from an atlas of the brain that may be prepared from an MR image of the brain. The atlas contains anatomical information of tissues both visible and not visible in the CT image. The image data in the atlas may be referenced to the Talairach coordinate system. The atlas is aligned to the CT image and the coordinate system of the CT image data is transformed to the Talairach coordinate system. The alignment of the CT image and the atlas may be performed using anatomical landmarks that are visible on both the CT image and the atlas. The CT image is then labeled automatically with the anatomical information in the atlas. The CT image may then be segmented based on the anatomical labeling.

DRAWINGS

These and other features, aspects, and advantages of the present invention will become better understood when the following detailed description is read with reference to the accompanying drawings in which like characters represent like parts throughout the drawings, wherein:

FIG. 6 is a cross-sectional image of an MR atlas of the brain taken along the coronal plane, in accordance with an exemplary embodiment of the present technique;

FIG. 7 is a cross-sectional image of an MR atlas of the brain taken along the sagittal plane, in accordance with an exemplary embodiment of the present technique;

FIG. 8 is a cross-sectional image of an MR atlas of the brain taken along the transverse plane, in accordance with an exemplary embodiment of the present technique;

FIG. 9 is a representation of the cross-sectional image of an MR atlas of the brain along the coronal plane of FIG. 6 being overlaid on the cross-sectional image of the brain along the coronal plane taken with a CT imaging system of FIG. 3, in accordance with an exemplary embodiment of the present technique;

FIG. 10 is a representation of the cross-sectional image of an MR atlas of the brain taken along the sagittal plane of FIG.

Figures 3, 4:
FIG. 3 is a cross-sectional image of the brain along the coronal plane taken with a CT imaging system, in accordance with an exemplary embodiment of the present technique.
FIG. 4 is a cross-sectional image of the brain along the sagittal plane taken with a CT imaging system, in accordance with an exemplary embodiment of the present technique.
Figure 5:
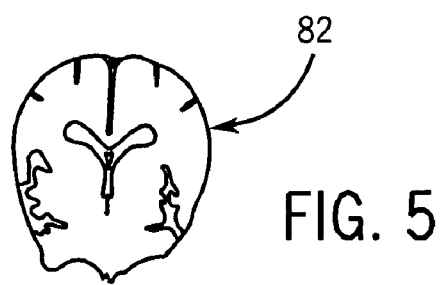
FIG. 5 is a cross-sectional image of the brain along the transverse plane taken with a CT imaging system, in accordance with an exemplary embodiment of the present technique.
Figure 12:
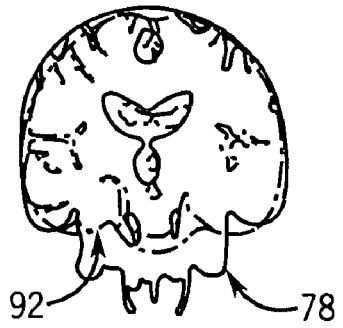
Figure 13:
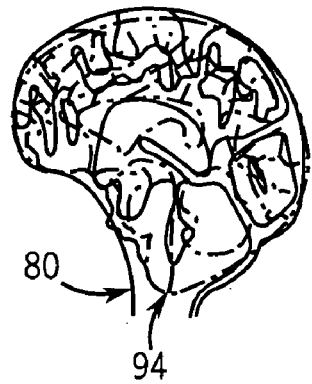
Figure 14:
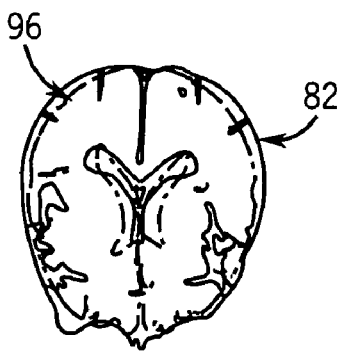
Figure 15:
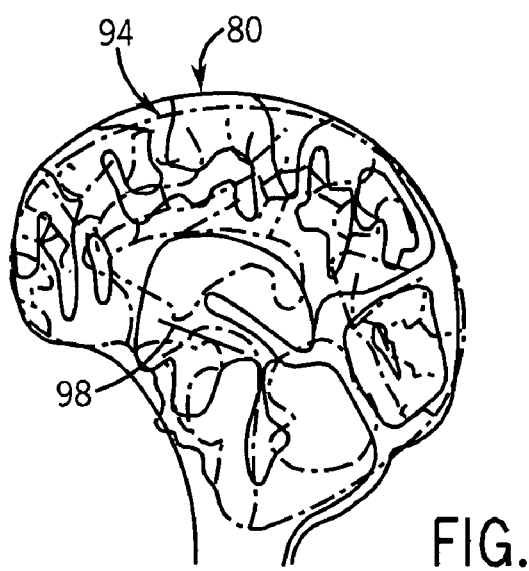

7 being overlaid on the cross-sectional image of the brain along the sagittal plane taken with a CT imaging system of FIG. 4, in accordance with an exemplary embodiment of the present technique;

FIG. 11 is a representation of the cross-sectional image of an MR atlas of the brain taken along the transverse plane of FIG. 8 being overlaid on the cross-sectional image of the brain along the transverse plane taken with a CT imaging system of FIG. 5, in accordance with an exemplary embodiment of the present technique;

FIG. 12 is a representation of the cross-sectional image of an MR atlas of the brain along the coronal plane of FIG. 6 registered with the cross-sectional image of the brain along the coronal plane taken with a CT imaging system of FIG. 3, in accordance with an exemplary embodiment of the present technique;

FIG. 13 is a representation of the cross-sectional image of an MR atlas of the brain taken along the sagittal plane of FIG. 7 registered with the cross-sectional image of the brain along the sagittal plane taken with a CT imaging system of FIG. 4, in accordance with an exemplary embodiment of the present technique;

FIG. 14 is a representation of the cross-sectional image of an MR atlas of the brain taken along the transverse plane of FIG. 8 registered with the cross-sectional image of the brain along the transverse plane taken with a CT imaging system of FIG. 5, in accordance with an exemplary embodiment of the present technique; and FIG. 15 is an enlarged view of FIG. 13 illustrating a line extending from the anterior commissure to the posterior commissure, in accordance with an exemplary embodiment of the present technique.

DETAILED DESCRIPTION

Figure 1:
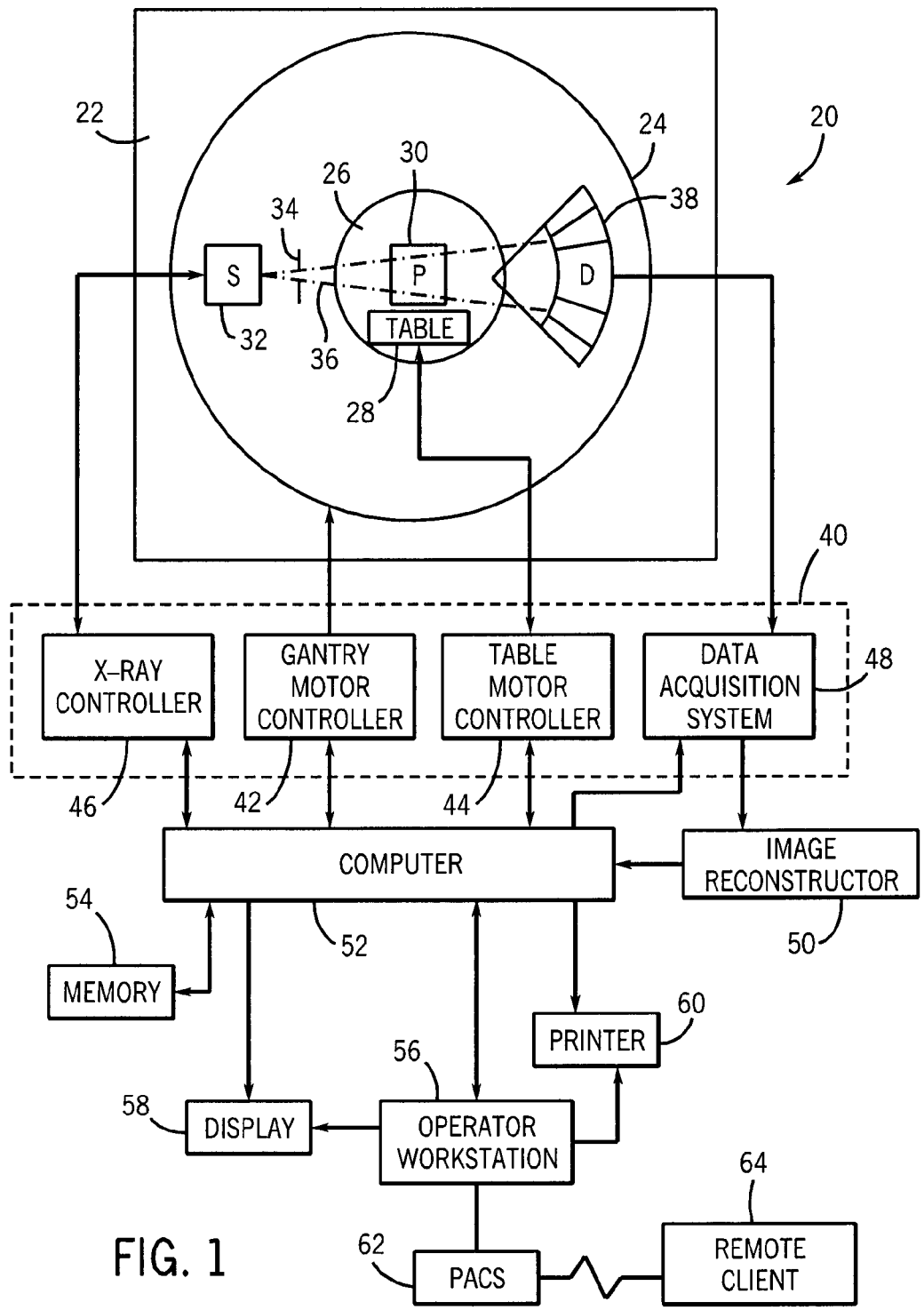
FIG. 1 is a diagrammatical view of an exemplary imaging system in the form of a CT imaging system adapted to use an MR atlas to produce processed images, in accordance with an exemplary embodiment of the present technique.

Referring now to FIG. 1, a computed tomography (CT) imaging system designed both to acquire original image data and to process the image data for display and analysis is presented, and referenced generally by reference numeral 20. The illustrated embodiment of the CT imaging system 20 has a frame 22, a gantry 24, and an aperture (imaging volume or CT bore volume) 26. A patient table 28 is positioned in the aperture 26 of the frame 22 and the gantry 24. The patient table 28 is adapted so that a patient 30 may recline comfortably during the examination process.

The illustrated embodiment of the CT imaging system 20 has an X-ray source 32 positioned adjacent to a collimator 34 that defines the size and shape of the X-ray beam 36 that emerges from the X-ray source 32. In typical operation, the X-ray source 32 projects a stream of radiation (an X-ray beam) 36 towards a detector array 38 mounted on the opposite side of the gantry 24. All or part of the X-ray beam 36 passes through a subject, such as a human patient 30, prior to impacting the detector array 38. It should be noted that all or part of the X-ray beam 36 may traverse a particular region of the patient 30, such as the liver, pancreas, heart, and so on, to allow a scan of the region to be acquired. The detector array 38 may be a single slice detector or a multi-slice detector and is generally formed by a plurality of detector elements. Each detector element produces an electrical signal that represents the intensity of the incident X-ray beam 36 at the detector element when the X-ray beam 36 strikes the detector array 38. These signals are acquired and processed to reconstruct an image of the features within the patient 30.

The gantry 24 may be rotated around the patient 30 so that a plurality of radiographic views may be collected along an imaging trajectory described by the motion of the X-ray source 32 relative to the patient 30. In particular, as the X-ray source 32 and the detector array 38 rotate along with the CT gantry 24, the detector array 38 collects data of X-ray beam attenuation at the various view angles relative to the patient 30. Data collected from the detector array 38 then undergoes pre-processing and calibration to condition the data to represent the line integrals of the attenuation coefficients of the scanned patient 30. The processed data, commonly called projections, are then filtered and back projected to formulate an image of the scanned area. Thus, an image or slice is acquired which may incorporate, in certain modes, less or more than 360 degrees of projection data, to formulate an image.

Rotation of the gantry 24 and operation of the X-ray source 32 is controlled by a system controller 40, which furnishes both power and control signals for CT examination sequences. Moreover, the detector array 38 is coupled to the system controller 40, which commands acquisition of the signals generated in the detector array 38. The system controller 40 may also execute various signal processing and filtration functions, such as for initial adjustment of dynamic ranges, interleaving of digital image data, and so forth. In general, system controller 40 commands operation of the imaging system 20 to execute examination protocols and to process acquired data. In the present context, system controller 40 also includes signal processing circuitry, typically based upon a general purpose or application-specific digital computer, associated memory circuitry for storing programs and routines executed by the computer, as well as configuration parameters and image data, interface circuits, and so forth. The system controller 40 includes a gantry motor controller 42 that controls the rotational speed and position of the gantry 24 and a table motor controller 44 that controls the linear displacement of the patient table 28 within the aperture 26. In this manner, the gantry motor controller 42 rotates the gantry 24, thereby rotating the X-ray source 32, collimator 34 and the detector array 38 one or multiple turns around the patient 30. Similarly, the table motor controller 44 displaces the patient table 28, and thus the patient 30, linearly within the aperture 26. Additionally, the X-ray source 32 may be controlled by an X-ray controller 46 disposed within the system controller 40. Particularly, the X-ray controller 46 may be configured to provide power and timing signals to the X-ray source 32.

In the illustrated embodiment, the system controller 40 also includes a data acquisition system 48. In this exemplary embodiment, the detector array 38 is coupled to the system controller 40, and more particularly to the data acquisition system 48. The data acquisition system 48 typically receives sampled analog signals from the detector array 38 and converts the data to digital signals for subsequent processing. An image reconstructor 50 coupled to the computer 52 may receive sampled and digitized data from the data acquisition system 48 and performs high-speed image reconstruction. Alternatively, reconstruction of the image may be done by the computer 52. Once reconstructed, the image produced by the imaging system 10 reveals internal features of the patient 30.

The data collected by the data acquisition system 48, or the reconstructed images, may be transmitted to the computer 52 and to a memory 54. It should be understood that any type of memory to store a large amount of data may be utilized by such an exemplary imaging system 10. Also the computer 52 may be configured to receive commands and scanning parameters from an operator via an operator workstation 56 typically equipped with a keyboard and other input devices. An operator may control the CT imaging system 20 via the operator workstation 56. Thus, the operator may observe the reconstructed image and other data relevant to the system from computer 52, initiate imaging, and so forth.

The CT imaging system 20 also has a display 58 that is coupled to the operator workstation 56 and the computer 52 and may be utilized by a user to observe the reconstructed image, as well as to provide an interface for control of the operation of the CT imaging system 20. In this embodiment, a printer 60 is present to enable a hard copy of a medical image to be printed. The operator workstation 56 may also be coupled to a picture archiving and communications system (PACS) 62. It should be noted that PACS 62 may be coupled to a remote system 64, such as radiology department information system (RIS), hospital information system (HIS) or to an internal or external network, so that others at different locations may gain access to the image and to the image data.

It should be further noted that the computer 52 and operator workstation 56 may be coupled to other output devices, such as a standard or special purpose computer monitor and associated processing circuitry. One or more operator workstations 56 may be further linked in the CT imaging system 20 for outputting system parameters, requesting examinations, viewing images, and so forth. In general, displays, printers, workstations, and similar devices supplied within the CT imaging system 20 may be local to the data acquisition components, or may be remote from these components, such as elsewhere within an institution or hospital, or in an entirely different location, linked to the imaging system CT via one or more configurable networks, such as the Internet, virtual private networks, and so forth.

CT imaging systems have been useful in the diagnosis of many medical conditions, such as strokes. "Stroke" is a generic term that is used to represent any one or all of a group of disorders, including cerebral infarction, intracerebral hemorrhage, or subarachnoid hemorrhage that can be characterized as a reduction in blood flow and volume in the cerebral region. For example, a cerebral infarction is an area of coagulation necrosis in brain tissue, (i.e., tissue death), that is due to local anemia resulting from an obstruction of the circulation to the area.

CT perfusion imaging is an example of a medical imaging technique. CT perfusion imaging allows absolute regional measurements of cerebral blood flow (CBF), cerebral blood volume (CBV), and mean transit time (MTT). Color-coded maps of these parameters can be produced for comparison against normal values. Threshold values of these parameters have been established to distinguish a cerebral infarction from normal brain tissue. However, using thresholds for reversible cerebral ischemia can be difficult as there is an overlap between the penumbral grey matter blood flow and normal white matter blood flow. Hence there is a need for differentiating between grey and white matter before thresholds can be applied. However, due to poor contrast, separating gray and white matter of the brain is challenging in CT imaging for both the radiologist and the computer application. As a result, every CT perfusion scan typically is accompanied by a full-brain non-contrast CT scan.

However, MR imaging is better able to distinguish deep brain tissues than CT imaging. A technique for supplementing a CT image of the brain with anatomical information obtained from an MR image is described below.

Figure 2:
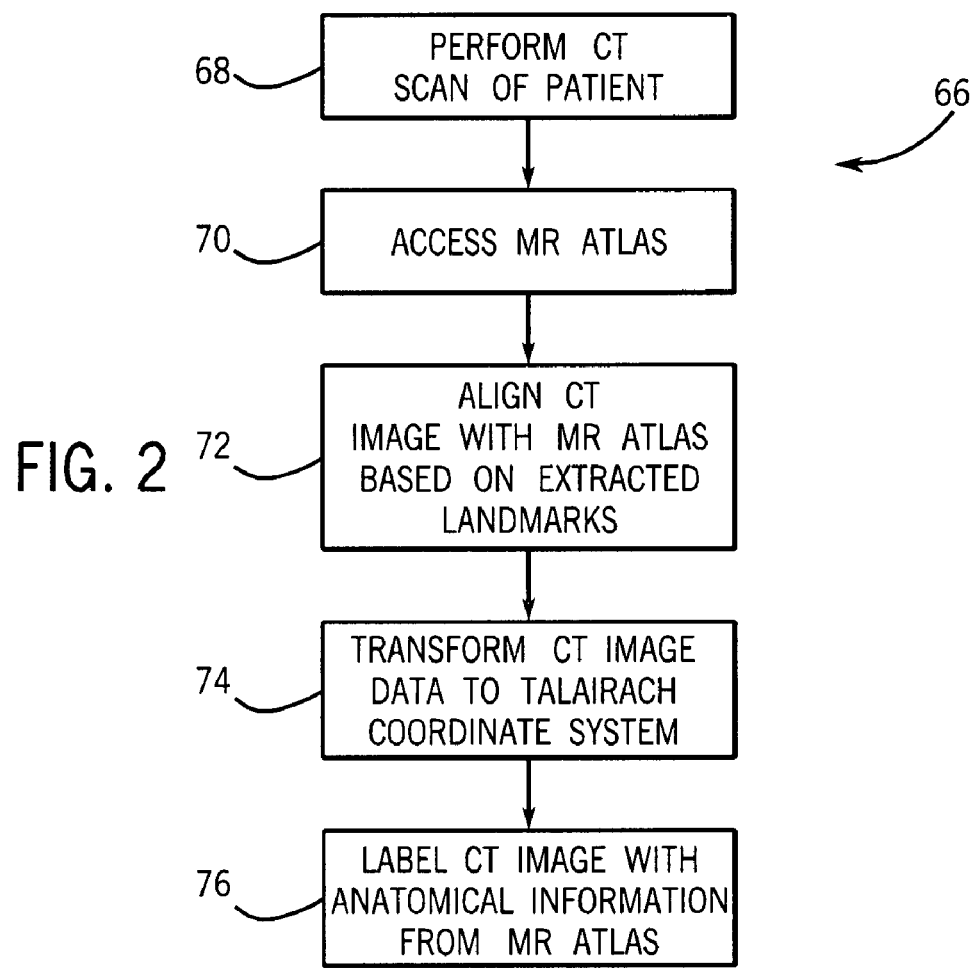
FIG. 2 is a block diagram of a technique for labeling a CT image with anatomical information from an MR atlas, in accordance with an exemplary embodiment of the present technique.

Referring generally to FIG. 2, an exemplary embodiment of a technique to label a CT image of the brain automatically with anatomical information obtained from an atlas of the brain is presented, and represented generally by reference numeral 66. The atlas of the brain may be prepared from an MR image of a brain. Hereinafter, the atlas is referred to as "MR atlas". The anatomical labeling of the CT image can then be used to facilitate the segmentation of the brain tissues, if desired. This technique is applicable to other portions of the body, as well. It should be noted that the present technique may be employed with brain maps and atlases created by other means than through MR imaging. Accordingly, the term "MR atlas" should not be understood as limiting the invention to use with a brain atlas generated exclusively through reference to MR images.

In the illustrated embodiment of the technique, a CT scan of the patient's brain is taken with the CT imaging system 20 to obtain a CT image of the patient's brain, as represented generally by block 68. A full-brain non-contrast CT scan is performed followed by a limited coverage CT perfusion. In this embodiment, the non-contrast scan is used for alignment with the MR atlas.

The MR atlas is then accessed by the CT imaging system 20, represented generally by block 70. The MR atlas may be prepared from an MR image of the brain. The MR atlas may be stored in memory within the CT imaging system 20, or it may be accessed from a remote location. Tissues that are not visible in the CT image are visible in the MR image, such as the deep tissues of the brain. The MR image is examined by a radiologist who manually provides the anatomical information to the MR image to form the atlas. The MR atlas contains anatomical information for tissues that are visible in the CT image and for tissues that are not visible in the CT image. In this embodiment, this MR atlas contains tissue classification information for the tissues of the brain. For example, the MR atlas contains information that identifies the gray matter of the brain as gray matter and the white matter of the brain as white matter. In addition, information other than tissue classification information may be provided, such as the names of various anatomical features, and other pertinent anatomical information.

The image data in the MR atlas is registered to the Talairach coordinate system of the brain, or Talairach atlas. The Talairach atlas is a three-dimensional coordinate system (having x, y, and z coordinates) that is used to describe the location of brain structures independent from individual differences in the size and overall shape of the brain. The Talairach space uses the anterior commissure ("AC") and the posterior commissure ("PC") of the brain as reference points. As noted above, the anterior and posterior commissures are fiber tracts that connect the two hemispheres of the brain. The AC is the origin of the Talairach atlas (having coordinate 0, 0, 0). A line extending from the AC to the PC ("the AC-PC line") defines the plane where z=0. Since these structures can be easily identified on MR images, it is easy to align an MR atlas to the Talairach atlas based on the AC-PC line. However, the scanned image obtained by the CT imaging system 20 is not aligned with the Talairach space because neither the AC, the PC, nor the AC-PC line are visible on a CT image. This problem is overcome in the present embodiment by aligning the MR atlas and the CT image, as described below. However, a coordinate system other than the Talairach coordinate system may be used by the atlas. For example, the RAS (right-anterior-superior) coordinate system or the RPS (right-posterior-superior) coordinate system may be used. More applicably to the brain, the Schaltenbrand-Warren (SW) brain atlas may be used.

Once the CT image and the MR atlas are accessed, the MR atlas is aligned to the CT image by the CT imaging system 20, represented generally by block 72. The alignment is initially done globally using a rigid or affine transform followed by a piece-wise affine correction constrained by the Talairach coordinates. Constraining the CT image data to the Talairach coordinate system requires invariant landmarks in the brain interior. In this embodiment of the technique, specific external and internal landmarks that are correlated to the AC-PC line are used, such as the posterior nasal spine, the vomer sphenoid junction, the basion, the opisthion, the anterior sphenoid spine, and the sella turcica. These points are used to scale the CT image to the size of the MR atlas. Six points are marked to locate the extent in each of the three dimensions: coronal, sagittal, and transverse. The cubic volume bounded by these six markers is divided into twelve regions and each region is scaled to match with the MR atlas.

Once aligned with the MR atlas, the CT image data is then transformed to correspond to the Talairach coordinate system of the MR atlas, represented generally by block 74. The AC-PC line from the MR atlas may be used as a reference for transforming the CT image data to the Talairach coordinate system.

Once aligned, the CT image is then labeled with the anatomical information from the MR atlas, as referenced generally by reference numeral 76. For example, brain tissues that are visible on the CT image are labeled automatically with tissue classification information. In addition, brain tissues that are not visible on the CT image, but are visible on the MR atlas, are also labeled with tissue classification information on the CT image. Thus, a radiologist examining the CT image can identify the tissues occupying a space in the CT image using the labeling information, even though the tissues themselves are not visible in the CT image, or are not distinguishable from other tissues. For example, the tissue classification information may enable a radiologist to distinguish the gray matter of the brain from the white matter. The labeling of the image with anatomical information also enables this information to be used in a segmentation routine. Thus, for example, the gray matter of the brain may be segmented from the white matter, and vice versa. As noted above, the anatomical information may be information other than tissue classification information.

Referring generally to FIGS. 3-5, examples of brain CT image slices taken from three planes through the brain are presented. As noted above, the CT imaging system 20 is operable to produce image slices at any angle through the patient's body. In these examples, the CT image slices were taken at three basic anatomical reference planes through the brain: the coronal plane, the saggittal plane, and the transverse plane. The coronal plane divides the brain into front and back portions. The sagittal plane divides the brain into left and right portions. Finally, the transverse plane divides the brain into top and bottom portions. FIG. 3 is a CT image slice, represented generally by reference numeral 78, taken along the coronal plane of the brain. FIG. 4 is a CT image slice, represented generally by reference numeral 80, taken along the saggittal plane of the brain. FIG. 5 is a CT image slice, represented generally by reference numeral 82, taken along the transverse plane of the brain.

Referring generally to FIGS. 6-8, examples of MR atlas image slices taken at three planes through the brain of the MR atlas are presented. FIG. 6 is an MR atlas image slice, represented generally by reference numeral 84, taken along the coronal plane of the brain. FIG. 7 is an MR atlas image slice, represented generally by reference numeral 86, taken along the saggittal plane of the brain. FIG. 8 is an MR atlas image slice, represented generally by reference numeral 88, taken along the transverse plane of the brain. The MR atlas is adapted with a visualization of the AC-PC line 90 that is visible in FIG. 7.

Referring generally to FIGS. 9-11, the MR brain atlas slices are overlaid onto their corresponding brain CT image slices. Prior to alignment, there are visible mismatches between the various MR brain atlas slices and the brain CT image slices.

Referring generally to FIGS. 12-14, examples of the MR brain atlas and CT image after alignment with the brain CT image slices are presented. The alignment algorithms of the CT imaging system 20 align the MR brain atlas onto the brain in the CT image in all three-dimensions. This is a deforming alignment, in which the shape of the MR atlas is changed to conform to the brain in the CT image. This is reflected in these images taken through the coronal, saggittal, and transverse planes of the now-aligned MR atlas and CT image of the brain. In FIG. 12, taken along the coronal plane, an aligned MR atlas image slice, represented generally by reference numeral 92, is shown aligned with the CT image. In FIG. 13, taken along the saggittal plane of the brain, the now-aligned MR atlas image slice, represented generally by reference numeral 94, is shown aligned with the CT image. In FIG. 14, taken along the transverse plane of the brain, a now-aligned MR atlas image slice, represented generally by reference numeral 96 is shown aligned with a CT image slice.

Referring generally to FIG. 15, an enlarged view of FIG. 13 is shown. This view illustrates the AC-PC line 98 of the now-aligned MR atlas. Once aligned, the anatomical labeling information may be transferred from the MR atlas to the CT image. The AC-PC line 98 may be transferred onto the CT image slice for transforming the frame of reference of the CT image data.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method of processing medical image data, comprising:
   accessing a computed tomography image of a brain;
   accessing an atlas having anatomical information referenced to a coordinate system, wherein the atlas comprises brain images taken with a magnetic resonance imaging system;
   aligning the computed tomography image with the atlas, wherein aligning the computed tomography image with the atlas comprises aligning using a rigid or affine transform followed by a piece-wise affine correction constrained by the coordinate system;
   transforming the computed tomography image to the coordinate system of the atlas; and
   labeling the computed tomography image with the anatomical information from the atlas.

2. The computer-implemented method as recited in claim 1, wherein the coordinate system is the Talairach coordinate system.

3. The computer-implemented method as recited in claim 2, comprising:
   transforming the computed tomography image data to the Talairach coordinate system.

4. The computer-implemented method as recited in claim 1, wherein the anatomical information from the atlas comprises brain tissue classification information.

5. The computer-implemented method as recited in claim 1, comprising:
   segmenting the computed tomography image based on the anatomical information from the atlas.

6. The computer-implemented method as recited in claim 1, wherein aligning the computed tomography image with the atlas comprises aligning the computed tomography image to a line between the anterior commissure and posterior commissure of the atlas.

7. The computer-implemented method as recited in claim 6, wherein aligning the computed tomography image to a line between the anterior commissure and posterior commissure of the atlas is based on aligning a plurality of landmarks visible on the computed tomography image to corresponding landmarks of the atlas.

8. The computer-implemented method as recited in claim 7, wherein the plurality of landmarks comprise anatomical features internal of the brain and external of the brain.

9. The computer-implemented method as recited in claim 1, wherein the brain image is labeled with anatomical information.

10. A system for processing medical image data, comprising:
    means for accessing a computed tomography image of a brain;
    means for accessing an atlas having anatomical information referenced to a coordinate system;
    means for aligning the computed tomography image with the atlas, wherein the atlas comprises brain images taken with a magnetic resonance imaging system, and wherein the means for aligning the computed tomography image with the atlas comprises aligning using a rigid or affine transform followed by a piece-wise affine correction constrained by the coordinate system;
    means for transforming the computed tomography image to the coordinate system of the atlas; and
    means for labeling the computed tomography image with the anatomical information from the atlas.

11. A non-transitory machine-readable medium for processing medical image data, comprising:
    code operable to access a computed tomography image of a brain;
    code operable to access an atlas having anatomical information referenced to a coordinate system, wherein the atlas comprises brain images taken with a magnetic resonance imaging system;
    code operable to align the computed tomography image with the atlas, wherein aligning the computed tomography image with the atlas comprises aligning using a rigid or affine transform followed by a piece-wise affine correction constrained by the coordinate system;
    code operable to transform the computed tomography image to the coordinate system of the atlas; and
    code operable to label the computed tomography image with the anatomical information from the atlas.

12. A computer-implemented method of processing medical image data, comprising:
    accessing computed tomography image data;
    accessing an atlas having tissue classification information referenced to a coordinate system, wherein the atlas comprises images taken with a magnetic resonance imaging system;
    aligning the computed tomography image data with the atlas using a rigid or affine transform followed by a piece-wise affine correction constrained by the coordinate system;
    transforming the computed tomography image data to the coordinate system of the atlas; and
    labeling the computed tomography image data with tissue classification information.

13. The computer-implemented method as recited in claim 12, wherein the atlas is referenced to the Talairach coordinate system.

14. The computer-implemented method as recited in claim 13, comprising:
    transforming the computed tomography image data to the Talairach coordinate system.

15. The computer-implemented method as recited in claim 12, wherein aligning the atlas with the computed tomography image data comprises aligning the atlas with the computed tomography image data based on a plurality of landmarks visible on the computed tomography image and the atlas.

16. The computer-implemented method as recited in claim 12, wherein the plurality of landmarks comprise anatomical features internal and external to the brain.

17. The computer-implemented method as recited in claim 12, comprising:
    segmenting the computed tomography image data based on the tissue classification information from the atlas.

18. A system for processing medical image data, comprising:
    means for accessing computed tomography image data;
    means for accessing an atlas having tissue classification information referenced to a coordinate system, wherein the atlas comprises images taken with a magnetic resonance imaging system;
    means for aligning the computed tomography image data with the atlas using a rigid or affine transform followed by a piece-wise affine correction constrained by the coordinate system;
    transforming the computed tomography image data to the coordinate system of the atlas; and
    means for labeling the computed tomography image data with the tissue classification information.

19. A non-transitory machine-readable medium for processing medical image data, comprising:
    code operable to access computed tomography image data;
    code operable to align the computed tomography image with the atlas using a rigid or affine transform followed by a piece-wise affine correction constrained by the coordinate system;
    code operable to transform the computed tomography image to the coordinate system of an atlas, wherein the atlas comprises images taken with a magnetic resonance imaging system; and
    code operable to label the computed tomography image data with tissue classification information.

20. The non-transitory machine-readable medium of claim 11, wherein the code operable to align the computed tomography image with the atlas comprises an affine or rigid transform.

* * * * *